(12) United States Patent
Klint

(10) Patent No.: US 6,458,137 B1
(45) Date of Patent: Oct. 1, 2002

(54) ASSEMBLY FOR POSITIONING AN EMBOLIZATION COIL IN THE VASCULAR SYSTEM AND A METHOD OF INTRODUCING A DETACHABLE EMBOLIZATION COIL

(75) Inventor: Henrik S. Klint, Lyngby (DK)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 09/577,777

(22) Filed: May 24, 2000

Related U.S. Application Data

(60) Provisional application No. 60/135,879, filed on May 26, 1999.

(51) Int. Cl.$^7$ .............................................. A61B 17/00
(52) U.S. Cl. ................................................ 606/108
(58) Field of Search .......................... 606/108, 198, 606/191, 194, 200, 1, 157, 151; 600/585, 434

(56) References Cited

U.S. PATENT DOCUMENTS

| | | |
|---|---|---|
| 5,122,136 A | 6/1992 | Guglielmi et al. |
| 5,234,437 A | 8/1993 | Sepetka |
| 5,250,071 A | 10/1993 | Palermo |
| 5,261,916 A | 11/1993 | Engelson |
| 5,358,479 A | 10/1994 | Wilson |
| 5,540,680 A | 7/1996 | Guglielmi et al. |
| 5,725,534 A | 3/1998 | Rasmussen |
| 5,964,771 A | * 10/1999 | Beyar et al. ................ 606/108 |

FOREIGN PATENT DOCUMENTS

| | | |
|---|---|---|
| EP | 0717969 | 6/1996 |
| EP | 0720838 | 7/1996 |
| WO | 9311823 | 6/1993 |
| WO | 9311825 | 6/1993 |
| WO | 9406502 | 3/1994 |
| WO | 9600104 | 1/1996 |

OTHER PUBLICATIONS

Cook Incorporated Brochures, "Detachable Embolization Coils", 4 pages; Bloomington, Indiana, 1996.
Cook Incorporated Brochures, "Embolization Microcoils", 2 pages; Bloomington, Indiana 1995.
Cook Incorporated Brochures, "Hilal Embolization Microcoils", 4 pages; Bloomington, Indiana 1988.

* cited by examiner

*Primary Examiner*—Kevin T. Truong
(74) *Attorney, Agent, or Firm*—Brinks Hofer Gilson & Lione

(57) ABSTRACT

An assembly for positioning an embolization coil (29) in the vascular system. The assembly comprises a delivery wire (1) having a central core (4) with a blade-shaped portion (10) which extends inside a threading coil (8) and has a blade thickness of preferably less than 40% of the blade width. The threading coil (8) is fixed to the central core at least at the edges of the blade-shaped portion.

25 Claims, 2 Drawing Sheets

ASSEMBLY FOR POSITIONING AN EMBOLIZATION COIL IN THE VASCULAR SYSTEM AND A METHOD OF INTRODUCING A DETACHABLE EMBOLIZATION COIL

RELATED APPLICATION INFORMATION

This relates to U.S. Provisional Patent Application Ser. No. 60/135,879 filed May 26, 1999.

FIELD OF THE INVENTION

The present invention relates to the field of medical devices and more particularly to embolization coils.

BACKGROUND OF THE INVENTION

The present invention relates to an assembly for positioning an embolization coil in the vascular system, comprising a delivery wire having a distal section with a central core and a threading coil fixed to the central core.

An assembly of this kind is known from U.S. Pat. No. 5,725,534 in which the threading coil is fixed on a cylindrical distal end portion of a guidewire core member. The distal end portion has a diameter corresponding to the inner diameter of the threading coil. Due to the relatively large diameter of the core, the core can have a relatively high rigidity which renders it difficult to advance the embolization coil to deployment sites in very narrow blood vessels that require access via tortuous paths.

A number of other methods for controlled release of embolization coils are known. WO 93/11823 describes an assembly in which the core at its distal end has two axially spaced soldered-on radial enlargements that lock coil ends to the core. In both WO 93/11825 and U.S. Pat. No. 5,250,071 a releasable geometrical locking is used between the coil and the guidewire, and in U.S. Pat. No. 5,122,136 the coil is affixed to the guidewire at thin connecting areas which are electrolytically eroded away when the coil is positioned at the desired site.

SUMMARY OF THE INVENTION

The object of the present invention is to provide an assembly that can access small and remote vascular sites more easily for easy and secure placement of the embolization coil.

The assembly of the present invention is accordingly designed with a delivery wire having a distal section with a central core and a threading coil, the central core including a blade-shaped portion having a blade thickness measured between sides and a blade width measured between edges, the threading coil having turns arranged with a pitch and affixed to the central core at least at the edges of the blade-shaped portion, and the blade thickness being less than the blade width, such as between 10% and 60% and preferably being 40% or less thereof.

The blade-shaped portion carrying the threading coil is much more flexible and easy to bend in the thickness direction of the blade than in the direction of the width where the blade dimension is the largest. The blade-shaped portion is a distal end portion of the central core, and if it is subjected to a torque, the central core twists. When the delivery wire is advanced through a catheter and has to pass through a curvature, the bladeshaped portion touches the inner wall of the catheter and is subjected to a torque until the blade-shaped portion itself has turned with the direction of width transverse to the curvature. The result is that the bending occurs in the thickness direction which is most flexible. Fixation of the threading coil at the edges provides control of the positioning of the threads so that the un-threading of the embolization coil occurs very smoothly. This is especially so in cases where the coil is positioned at the delivery site in an oblique position with respect to the threading coil, which could have caused increased friction had the threaded coil been fixed on a cylindrical member.

In one embodiment, the blade width is less than the inner diameter of the threading coil, and this reduces the bending rigidity of the blade-shaped portion.

In another embodiment the edges of the blade-shaped portion are provided with recesses in which the turns of the threading coil are seated. These recesses can for example be laser-cut or etched into the blade-shaped portion. They provide a high security for locking of the threading coil, even if it is not fixed by other means than the geometrical interlocking of recesses and coil turns.

In embodiments where the threading coil is fixed by use of solder, the solder is positioned on at least one of the flat sides of the blade-shaped portion in a wave-shaped pattern, with the threading coil located on the wave crests and with the bottom of the wave troughs located less than a distance d from the flat side, where the distance d is at most ¼ of the inner diameter D of the threading coil. Even though the solder is a soft material without great resistance to bending, it is favorable to minimize the presence of the material so that the relatively high bending flexibility is retained in the direction of thickness of the blade-shaped portion. Extending the very deep wave troughs to positions close to the blade-shaped portion allows mutual flexure of the wave crests when the blade-shaped portion bends.

Preferably, the distal end of the threading coil terminates at a position less than twice the diameter of the threading coil wire from one of the flat sides of the blade-shaped portion. The threading coil wire has very diminutive dimensions and any permanent bending of its distal end can be detrimental to the functioning of the thread. By using a microscope it is possible to adjust the threading coil wire to terminate close to the flat side of the blade-shaped portion to which it is fixed. It is also an advantage that there is no lengthy, protruding threading coil wire end that could cause harm to vascular tissue.

The threading coil or the blade-shaped portion can be made of radiopaque material in order to be discerned on an image screen by the radiologist or neuroradiologist that introduces the detachable coil into the vascular system of a patient, but in order to be seen clearly it ought to have relatively large dimensions. The blade-shaped portion can be difficult to see if the image shows it in a sideview. This drawback of making the central core blade-shaped can be made up for by positioning a radiopaque marker at a predefined first distance, such as about 3 to 3.5 cm, proximal to the distal termination of the threading coil. In this embodiment it is not required for the threading coil or the blade-shaped member to be radiopaque, because the marker indicates the position from the first distance.

In a further development of the latter embodiment, the assembly includes a catheter having a distal delivery opening, with a radiopaque marker at a predetermined second distance proximal to the delivery opening; and the first distance on the delivery wire and the second distance on the catheter are such, that the distal termination of the threading coil is positioned at the delivery opening when the marker on the delivery wire is positioned at the marker on the catheter. By also including a marker on the catheter, the requirement for judging distances on a screen can to a large extent be dispensed with. In order to obtain correct positioning of the threading coil at the delivery opening all that is required is to advance the delivery wire until the marking on the wire is observed on the screen, to attain the predefined position relative to the marker on the catheter. If the markers have a short length, the predefined position can be one of mutual overlap; but in case the markers are longer, in order to be clearly visible it is preferred that the predefined position is attained when the distal edge of the marker on the delivery wire has been advanced exactly to the proximal edge of the marker on the catheter.

The security of the placement can be further improved by an embodiment in which a pin vise has fixing means for detachable fixing on the delivery wire and carries a cannula of a length of at least 8 cm through which the delivery wire is insertable. This pin vise can be placed at the proximal end of the catheter system prior to inserting the delivery wire. The length of the cannula ensures that it can extend through a Y-connector and a fitting mounted on the proximal end of the catheter. The distal end of the cannula is positioned in the catheter. When the delivery wire is inserted through the pin vise, fluid will flow out through the cannula outside the patient and clean the embolization coil and the delivery wire while these are introduced.

The present invention furthermore relates to a method of introducing a detachable embolization coil into a deployment site in the vascular system. According to the method of the present invention: a catheter system with a catheter having a radiopaque marker is positioned in the vascular system with its distal delivery opening at the deployment site and with the proximal end of the catheter system outside the patient; a delivery wire is advanced through the catheter until a radiopaque marker on the delivery wire is positioned at a radiopaque marker on the catheter; a pin vise is then positionally locked on the delivery wire in abutment against the proximal end of the catheter system; then, the pin vise is rotated in a detach direction until the embolization coil is detached from the delivery wire.

The method is safe to use because it assures in a convenient manner that the distal termination of the delivery wire is exactly at the delivery opening or on the proximal side thereof when the embolization coil is detached, so that on one hand the threading coil is unable to damage the vascular wall, and on the other hand the detached coil gets completely clear of the catheter and cannot be inadvertently pulled away from the deployment site when the delivery wire and the catheter are retracted from the vascular system.

BRIEF DESCRIPTION OF THE DRAWINGS

Examples of the invention will now be explained below by way of example with reference to the schematic drawings, in which.

DETAILED DESCRIPTION

Figure 1:
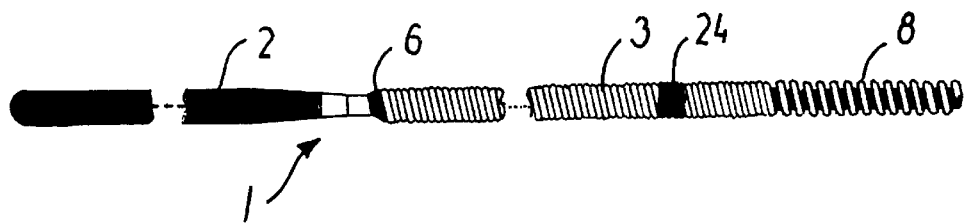
FIG. 1 depicts a sectional view of a delivery wire for an assembly according to the present invention, viewed from above.
Figure 2:
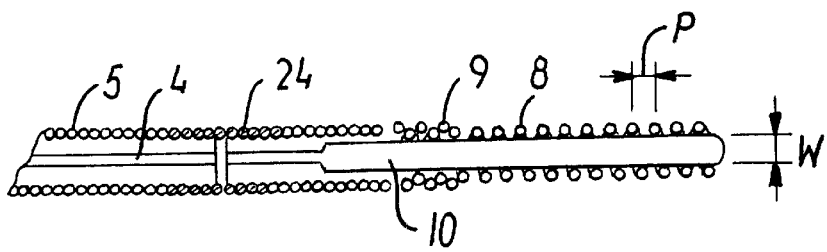
FIGS. 2 and 3 are enlarged sectional views of the distal end of the delivery wire in FIG. 1 viewed from above and from the side, respectively.

A delivery wire 1 shown in FIG. 1 has an elongated shaft segment 2 of stainless steel or of another suitable material, such as nitinol, having a length in the range of 50 to 250 cm and a diameter in the range of 0.20 to 2.0 mm, depending on the relevant field of application. The shaft segment may typically be made of a single wire or rod. In a distal section 3 the delivery wire is relatively more flexible and comprises a central core 4 (FIG. 2) of stainless steel or nitinol; a wire coil 5 mounted outside the core is fixed to core 4 at a proximal end 6 and fixed to a threading coil 8 at a distal end 9.

The central core 4 has at its distal end a blade-shaped portion 10 having a blade thickness t and a blade width w, where t is less than w. Blade thickness t should be between 10% and 60% of w, preferably between 15% and 40% and most preferably about 20% of w. The threading coil 8 is fixed on the blade-shaped portion, e.g. by soldering, welding, brazing or gluing. The solder can, for example, be tin, gold or silver solder. In case of gluing, plastic-based adhesives are preferred, and as examples can be mentioned a two-component adhesive "Activator No. 7649, adhesive No. 326" from Loctite, which cures on contact between the two components; an adhesive No. 3311 from Loctite; or an adhesive No. 136 from Dymax, where the two latter adhesives cure on irradiation with ultraviolet (UV) light. The threading coil wire can be of stainless steel and can have a wire diameter in the range of 0.02 to 0.12 mm, typically a diameter of about 0.075 mm. The wire is set with a pitch p corresponding to or being larger than twice the thickness of the wire so that a mating threading in the proximal end of a detachable embolization coil can be threaded into and out of the threading coil 8. The outer diameter of the threading coil can, for superselective use, be in the range of 0 to 1 mm, and typically, from 0.20 mm to 0.45 mm.

Preferably, the blade-shaped portion 10 and the threading coil 8 have dimensions so that from eight to twenty turns, and more preferably from ten to fourteen turns, are fixed on the blade-shaped portion.

Figure 3:
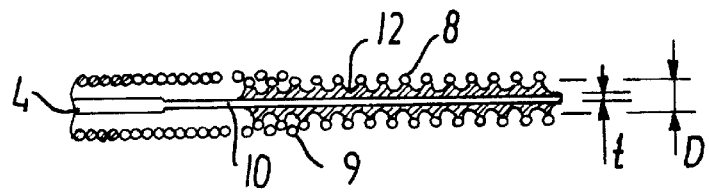
Figure 4:
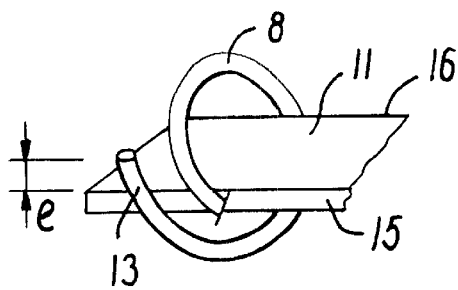
FIG. 4 is an enlarged sketch of the distal termination of the threading coil wire.
Figure 5:
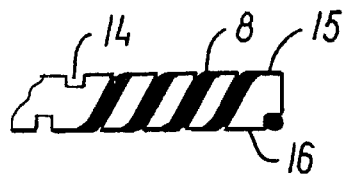
FIG. 5 is a partial view of the delivery wire of another embodiment.

The solder or brazing is applied on one or both of the flat sides 11 of the blade-shaped portion in a wave-shaped pattern which most clearly appears in FIG. 3. Threading coil 8 is located on the wave crests and the bottom of the wave troughs 12 is located at a short distance from the associated flat side. Distal end 13 of the threading coil terminates at a position that is located at a distance e having less than twice the diameter of the threading coil wire from the flat side 11. FIG. 4 depicts this position just before the coil is soldered or otherwise fixed to the bladeshaped portion. As an alternative or in addition to soldering or brazing, the threading coil 8 can be locked mechanically to the blade-shaped portion by seating the blade-shaped portion within recesses 14 in the edges 15,16. This can for example be effected by laser cutting the blade-shaped portion to the desired shape. Then the threading coil is positioned onto the blade-shaped portion with the turns of threading coil wire inserted into the recesses.

The delivery wire is shown to have a radiopaque marker 24 at a predetermined distance from the distal end of the threaded coil 8. The marker can be of platinum wire inserted into the wire of the coil 5, or it can be a separate member such as a platinum or gold ring.

Figure 6:
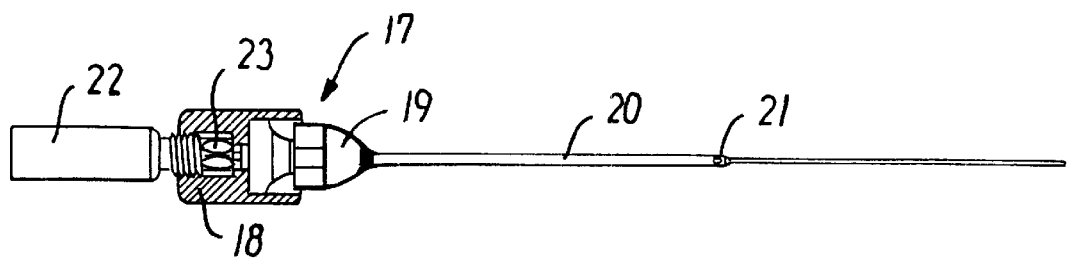
FIG. 6 is an enlarged view of a pin vise of the above mentioned embodiments.
Figure 7:
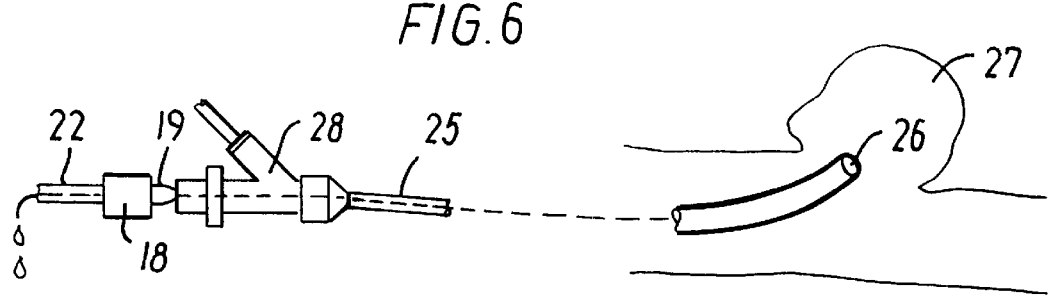
FIGS. 7–10 are illustrations of the method of placing an embolization coil with the assembly of FIGS. 1–6.

FIG. 6 shows a pin vise 17 for being releasably fixed to the delivery wire in order to enable turning the wire by hand when the detachable embolization coil is to be detached. Pin vise 17 includes a housing 18 with a holder 19 for a cannula 20 which in a first section has a larger inner diameter than the outer diameter of the delivery wire and in a second section has a smaller inner diameter just allowing the delivery wire to pass through the cannula. A hole 21 through the cannula wall in the first section establishes communication between the exterior and the interior of the cannula. Opposite to holder 19 the housing 18 has a tightening member 22 which can be screwed into an internally threaded bore in the housing, thereby causing a locking member 23 to radially compress a central channel running through the whole pin vise. When a delivery wire has been inserted through the central channel the pin vise thus locks onto the delivery wire. Turning in the opposite direction causes the pin vise to be released.

Now an example of the operation of the assembly is described in further detail with reference to FIGS. 7 to 10 in which the right hand sides of the drawings are enlarged in order to show more clearly the operation.

First of all, a catheter system with a catheter 25 is positioned in the vascular system of the patient with its distal delivery opening 26 at a deployment site 27 and with the proximal end of the catheter system outside the patient. On the proximal end the catheter has an Y-connector 28, and the cannula of the pin vise 17 has been inserted into the main leg of the Y-connector. A flushing fluid such as saline water is introduced through the other leg of the Y-connector. Due to the hole 21 in the cannula, fluid flows through the cannula in the proximal direction and drips out of the central channel.

Figure 8:
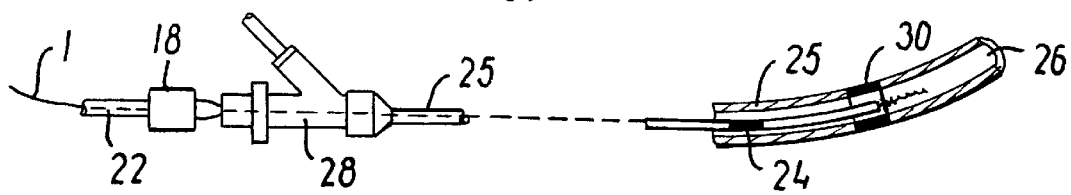
Figure 9:
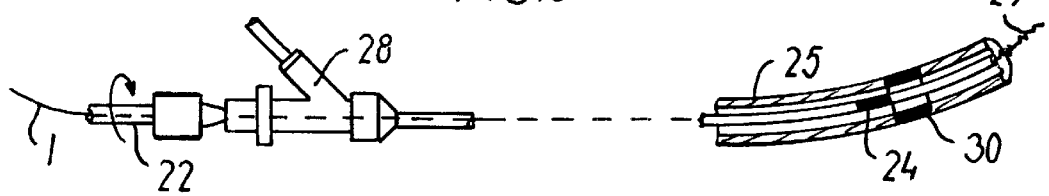

Then an introducer with the delivery wire 1 with the embolization (or occlusion) coil 29, is inserted through the pin vise until the introducer hits the transition between the first and the second section of cannula 20, and then the delivery wire with the coil is pushed onwards through the second section of the cannula and further on into the catheter, as depicted in FIG. 8. During the advancing through cannula 20, the fluid flowing in through the hole 21 flushes the embolization coil for air and any other unwanted impurities, thus promoting the secure placement of the coil in the patient. The physician follows the advancing of the delivery wire on a screen or monitor where the marker 24 is visible. When the radiopaque marker 24 on the delivery wire is positioned at a radiopaque marker 30 on the catheter, as shown in FIG. 9, then tightening member 22 is rotated to positionally lock the pin vise to the delivery wire in abutment against the proximal end of the catheter system.

Figure 10:

With the catheter and the delivery wire in position, it is rather easy to rotate the pin vise in a detach direction until the embolization coil detaches from the delivery wire (FIG. 10). During detachment the pin vise abuts the proximal end of Y-connecter so that the physician is prevented from inadvertently pushing the delivery wire out through the delivery opening in the catheter, which would otherwise involve a rather high risk of damaging the feeble vascular wall. When further coils are mounted on the same delivery wire, for detachment at the same site 27 the pin vise can be kept locked at the same position on the wire which is simply advanced through the catheter until the pin vise abuts the proximal end of the Y-connector 28.

Embolization coils are well-known in the art and can be produced from platinum or nitinol wire with coil lengths of between 5 and 3000 mm and having different geometries in the unloaded state, such as straight, arcuate, figure-eight-shaped or more complicated shapes. The internal coil diameter may typically range from 0.14 to 0.45 mm, preferably about 0.20 mm. In a preferred embodiment, the coil is made from a wire having a wire diameter of 0.075 mm, wound into an external coil diameter of about 0.38 mm (0.015 US inch). Regarding applicable geometries for embolization coils, please refer to the commercially available geometries for coils which are known, for example, from the company William Cook Europe under the trade names "Hilal Embolization Microcoils" and "MWCE Embolization Microcoils with Multiple Curls."

The above-described assembly of a delivery wire with an embolization coil and a catheter with an Y-connector and a pin vise can be modified in various manners within the scope of the following claims. It is possible to make the shaft segment 2 and the distal portion 3 of the delivery wire as a single shaft segment of several helically wound filaments having a much larger pitch than the threading coil 8.

The blade-shaped portion 10 carrying the threading coil 8 allows the delivery wire to bend easily and to self-adjust to curvatures, thus promoting safe and secure placement of the embolization coil.

What is claimed is:

1. An assembly for positioning an embolization coil in the vascular system, comprising a delivery wire which in a distal section has a central core and a threading coil fixed to the central core, wherein said threading coil has at least three distal turns arranged with a pitch allowing the embolization coil to be threaded in and out of the threading coil, wherein the central core has a blade-shaped portion that extends inside the threading coil and has a blade thickness, a blade width and edges, said blade thickness being less than the blade width, and wherein the threading coil is fixed to the central core at least at the edges of the blade-shaped portion.

2. An assembly according to claim 1, wherein said blade thickness is between 10% and 60% of the blade width.

3. An assembly according to claim 1, wherein said blade thickness is between 15% and 40% of the blade width.

4. An assembly according to claim 1, wherein said blade thickness is about 20% of the blade width.

5. An assembly according to claim 1, wherein said threading coil has an inner diameter, and the blade width is less than the inner diameter of the threading coil.

6. An assembly according to claim 1, wherein the edges of the blade-shaped portion are provided with recesses in which the threading coil is locked.

7. An assembly according to claim 6, wherein the blade-shaped portion has flat sides, said solder is positioned on at least one of the flat sides in a wave-shaped pattern having wave crests and wave troughs, said threading coil is located on the wave crests, a bottom of said wave troughs is located less than a distance d from said flat side, where the distance d is at the most ¼ of an inner diameter D of the threading coil.

8. An assembly according to claim 7, wherein the threading coil wire has a diameter, and the threading coil has a distal end terminating at a position less than twice the diameter of the threading coil wire from one of the flat sides of the blade-shaped portion.

9. An assembly according to claims 1, wherein the threading coil is fixed to the blade-shaped portion by solder or welding material.

10. An assembly according to claim 1, wherein a radiopaque marker is positioned at a predefined first distance, such as about 3 to 3.5 cm, proximal to the distal termination of the threading coil.

11. An assembly according to claim 10, wherein the assembly further includes a catheter having a distal delivery opening and at a predetermined second distance proximal to the delivery opening a radiopaque marker, and the first distance on the delivery wire and the second distance on the catheter are so that the distal termination of the threading coil is positioned at the delivery opening when the marker on the delivery wire is positioned at the marker on the catheter.

12. An assembly according to claim 10, wherein a pin vise has fixing means for detachable fixing on the delivery wire and carries a cannula of a length of at least 8 cm through which the delivery wire is insertable.

13. An assembly for positioning an embolization coil in a vascular system, wherein a delivery wire has a distal section with a central core and a threading coil, said central core including a blade-shaped portion having a blade thickness measured between sides and a blade width measured between edges, said threading coil having turns arranged with a pitch and fixed to the central core at least at the edges of the blade-shaped portion, and said blade thickness being less than the blade width.

14. An assembly according to claim 13, wherein said blade thickness is between 10% and 60% of the blade width.

15. An assembly according to claim 13, wherein said blade thickness is between 15% and 40% of the blade width.

16. An assembly according to claim 13, wherein said blade thickness is about 20% of the blade width.

17. An assembly according to claim 13, wherein solder or welding material fixes the threading coil to the blade-shaped portion.

18. An assembly according to claim 17, wherein the sides of the blade-shaped portion are flat, and the solder is positioned on at least one of the flat sides in a wave-shaped pattern having wave crests and wave troughs, said threading coil is located on the wave crests.

19. An assembly according to claim 18, wherein the threading coil has an inner diameter D, and bottoms of said wave troughs are located less than a distance d from said flat side, the distance d being at the most ¼ of said inner diameter D.

20. An assembly according to claim 19, wherein the threading coil wire has a diameter, and the threading coil has a distal end terminating at a position less than twice the diameter of the threading coil wire from one of the flat sides of the blade-shaped portion.

21. An assembly according to claim 19, wherein a radiopaque 20 marker is positioned at a predefined first distance, such as about 3 to 3.5 cm, proximal to the distal termination of the threading coil.

22. An assembly according to claim 21, wherein the assembly further includes a catheter having a distal delivery opening and at a predetermined second distance proximal to the delivery opening a radiopaque marker, and the first distance on the delivery wire and the second distance on the catheter are so that the distal termination of the threading coil is positioned at the delivery opening when the marker on the delivery wire is positioned at the marker on the catheter.

23. An assembly according to claim 22, wherein a pin vise has fixing means for detachable fixing on the delivery wire and carries a length of cannula through which the delivery wire is insertable.

24. A method of introducing a detachable embolization coil into a deployment site in a vascular system of a patient, comprising:
  positioning in the vascular system a catheter system with a catheter having a radiopaque marker, with a distal delivery opening of the catheter positioned at the deployment site and with a proximal end of the catheter system outside the patient;
  advancing a delivery wire through the catheter until a radiopaque marker on the delivery wire is positioned at a radiopaque marker on the catheter, wherein said delivery wire includes the assembly of claim 1;
  locking a pin vise on the delivery wire in abutment against the proximal end of the catheter system; and
  rotating the pin vise in a detach direction until the detachable embolization coil is detached the delivery wire.

25. The method of claim 24, wherein, during subsequent introduction of further embolization coils to the deployment site without removal of the catheter, the pin vise remains locked in position on the delivery wire.

* * * * *

UNITED STATES PATENT AND TRADEMARK OFFICE
CERTIFICATE OF CORRECTION

PATENT NO.    : 6,458,137 B1
DATED         : October 1, 2002
INVENTOR(S)   : Henrik S. Klint It is certified that error appears in the above-identified patent and that said Letters Patent is hereby corrected as shown below:

<u>Column 8,</u>
Line 4, delete "20".
Line 34, after "is detached" insert -- from --.

Signed and Sealed this

Twenty-ninth Day of July, 2003

JAMES E. ROGAN
*Director of the United States Patent and Trademark Office*